United States Patent [19]

Joos

[11] 4,150,012

[45] Apr. 17, 1979

[54] DISCERNIBLE DENTAL SEALANT

[75] Inventor: Richard W. Joos, Eagan, Minn.

[73] Assignee: Minnesota Mining and Manufacturing Company, St. Paul, Minn.

[21] Appl. No.: 761,116

[22] Filed: Jan. 21, 1977

[51] Int. Cl.$^2$ ............................................. C08K 9/06
[52] U.S. Cl. ...................................... 260/42.15; 32/15; 260/42.52; 260/42.57; 260/998; 260/11
[58] Field of Search ............... 260/42.15, 42.57, 42.52, 260/998, 11, DIG. 36; 32/15

[56] References Cited

U.S. PATENT DOCUMENTS

| | | | |
|---|---|---|---|
| 3,200,142 | 8/1965 | Bowen | 260/486 |
| 3,539,533 | 11/1970 | Lee et al. | 260/42.52 |
| 3,709,866 | 1/1973 | Waller | 260/42.52 |
| 3,815,239 | 6/1974 | Lee et al. | 260/42.52 |
| 3,835,090 | 9/1974 | Gander et al. | 260/42.15 |
| 3,853,962 | 12/1974 | Gander | 260/42.52 |
| 3,889,385 | 6/1975 | Dougherty | 32/12 |
| 3,926,906 | 12/1975 | Lee et al. | 260/42.15 |

*Primary Examiner*—Lewis T. Jacobs
*Attorney, Agent, or Firm*—Cruzan Alexander; D. M. Sell; D. P. Edmundson

[57] ABSTRACT

A composition and method adapted for discernibly filling and sealing pits and fissures in tooth surfaces is described. The novel compositions contain finely divided hydrophobic opaquing filler and hydrophobic suspending agent, in defined amounts, in a polymerizable resin system. Placement of the composition on dental surfaces is simplified and retention is easily verified.

15 Claims, No Drawings

DISCERNIBLE DENTAL SEALANT

BACKGROUND OF THE INVENTION

This invention relates to compositions and methods for sealing pits and fissures in tooth surfaces (i.e. dental enamel).

Almost all children are plagued with dental surface imperfections—commonly termed pits and fissures—which tend to harbor and permit proliferation of microorganisms which can cause formation of caries. Since normal dental hygiene methods such as tooth brushing are relatively ineffective against these physically protected microorganisms it has been the practice of many dentists for a considerable time to attempt to seal the pits and fissures so as to eliminate these sites for microorganism growth.

Commonly used pit and fissure sealants are composed of a polymerizable resin system, such as the polymerizable acrylic system described in U.S. Pat. No. 3,066,112 (Bowen), free of filler. The reason for the common use of a resin system free of filler is indicated by U.S. Pat. No. 3,815,239 (Lee et al.) which teaches that pit and fissure sealants must be of sufficiently low viscosity to be capable of flowing into the pits and fissures to assure complete sealing and good adhesion to the tooth surface.

A common drawback associated with such sealents which are free of filler is that they are transparent (or, at best, translucent) and consequently it is difficult for the dentist to ensure accurate placement and adequate coverage of pits and fissures when using such sealants. The placement difficulty reduces the effectiveness of the treatment itself because the dentist may not observe that some pits and fissures remain unsealed. Further, with respect to some other pits and fissures the dentist may apply much more sealant than necessary simply because of the difficulty in observing the sealant in place. Additionally, periodical re-checks by the dentist to replace worn or dislodged sealant or to apply additional sealant to newly developed pits and fissures are rendered difficult or uncertain because of the difficulty in ascertaining the presence or absence of such transparent or translucent sealings.

Although it might appear possible to provide a suitable discernible pit and fissure sealant by simply adding a pigment to a polymerizable resin, it has been found that the pigment easily settles out of the sealant upon standing. Accordingly, the sealant must either be stirred thoroughly prior to use or the pigment must be added to the resin system and stirred at each time of use.

Others have suggested the incorporation of an ultraviolet fluorescing dye into the polymerizable resin which can then be detected on a tooth surface under ultraviolet light. However, this technique requires the use of ultraviolet light and, furthermore, the dye may leach out of the sealant on the tooth with passage of time.

Similarly, simple dilution of commercially available dental restorative paste by addition of unfilled resin does not produce a desirable pit and fissure sealant because at low levels of dilution the material is too high in viscosity to penetrate adequately into pits and fissures, and at high levels of dilution the material is not sufficiently discernible on tooth surfaces.

The compositions and methods of the present invention are adapted for filling and sealing pits and fissures in tooth surfaces in a discernible manner.

SUMMARY OF THE INVENTION

In accordance with the present invention it has been found that pits and fissures in tooth surfaces may be filled and sealed in a discernible manner by the method comprising:

(a) applying to the tooth surfaces a composition comprising a polymerizable resin system, finely divided hydrophobic opaquing filler present in an amount of about 0.1 to 5% by weight based on the weight of the resin system, and hydrophobic suspending agent present in an amount of about 1 to 10% by weight based on the weight of the resin system, the composition having a viscosity not greater than about 600 centipoise when applied to the tooth surfaces; and (b) hardening the composition in situ to produce a discernible coating.

It has also been found that discernible, shelf-stable pit and fissure sealant compositions are those containing polymerizable resin, 0.1 to 5% by weight (based on resin weight) of hydrophobic opaquing filler, and 1 to 10% by weight (based on resin weight) of hydrophobic suspending agent. It is unexpected that such a composition could be prepared which would be (a) sufficiently fluid to be effective as a pit and fissure sealant, and (b) sufficiently opaque to be discernible on tooth surfaces, and (c) sufficiently shelf-stable at low viscosity to be commerically useful. It is also unexpected that the opaquing filler and the suspending agent must be rendered hydrophobic, and be present in the composition in proper amounts, in order to produce the results desired in the invention.

These compositions as applied to tooth surfaces are found to adhere very well and seal pits and fissures very effectively. These sealants are of sufficient contrast to the tooth that they can be easily and quickly placed by the dentist in an efficient manner. The sealant accordingly can be readily verified upon subsequent checkups of the patient and yet the sealant does not present an unsightly or objectionable appearance.

Furhtermore, the compositions of the invention exhibit prolonged shelf life without separation of the ingredients.

DETAILED DESCRIPTION OF THE INVENTION

The compositions useful in the present invention may be in various forms. For example, the composition may be composed of two fluid materials, each having a viscosity in the range of about 200 to 600 centipoise, disposed in separate containers from which a dentist may dispense necessary amounts of material which when mixed together will produce a sealant which is discernible on tooth surfaces. The material in the first of the containers consists essentially of polymerizable resin, finely divided hydrophobic opaquing filler in an amount of about 0.1 to 5% by weight (based on weight of resin), hydrophobic suspending agent in an amount of about 1 to 10% by weight (based on weight of resin), and catalyst; the material in the second of the containers consists essentially of polymerizable resin, finely divided hydrophobic opaquing filler in an amount of 0.1 to 5% by weight (based on weight of resin), hydrophobic suspending agent in an amount of about 1 to 10% by weight (based on weight of resin), and accelerator reactive with the catalyst in the first container.

In another embodiment the composition is in the form of two fluid materials, one of the fluid materials comprising polymerizable resin and either catalyst or accelerator while the other of said fluid materials comprises polymerizable resin, hydrophobic opaquing filler, hydrophobic suspending agent, and either catalyst (when the first fluid material contains accelerator) or accelerator (when the first fluid material contains catalyst).

The polymerizable resin which is suitable for use in the present invention may be any polymerizable material which is liquid and compatible with the conditions in the oral cavity and polymerizable therein (preferably without inconvenience to the patient) to a solid polymer having a glass transition temperature above the normal range of oral temperatures. It will preferably be adherent to tooth surfaces both before and after hardening.

Preferred types of polymerizable resins are acrylic monomers which are very well known for use in dental restorative materials. A presently preferred type of acrylic monomer is that described in U.S. Pat. No. 3,066,112, incorporated herein by reference. Such acrylic monomer is the reaction product of bisphenol A or other bisphenol with glycidyl methacrylate, the reaction product being commonly referred to in the art as Bis-GMA monomer. Typically this monomer or resin is desirably thinned by adding thereto various amounts of other monomers such as dimethacrylate monomers (e.g. tetraethyleneglycol dimethacrylate, ethyleneglycol dimethacrylate, triethyleneglycol dimethacrylate, etc.) or acrylate monomers (e.g. methyl methacrylate).

The opaquing filler used in the present invention is preferably finely divided titanium dioxide, although other non-toxic and non-irritating opaquing agents could also be used. Even those materials which are sometimes useful in other applications as transparent fillers can be used in the present invention as opaquing filler if it is of the correct particle size (i.e. about 0.1 to 1 micron). Examples of this type of opaquing filler are silicon dioxide and aluminum oxide. Glass may also be used.

The efficiency of the opaquing filler, and hence the amount of it which may be used, will vary depending upon the particle size distribution and upon the relative indices of refraction of the opaquing filler and the cured resin system. Generally speaking, the most efficient opaquing filler has a particle size in the range of about 0.2 to 0.7 micron; filler which has a broader particle size distribution may not be quite as efficient in terms of opaquing but still may be used. As a general rule, the greater the difference in index of refraction between the filler and the cured resin, the more efficient the filler is in terms of opaquing.

As stated, the preferred opaquing filler is titanium dioxide. It is also preferred that the titanium dioxide have a particle size in the range of about 0.1 to 2 microns. Preferably the titanium dioxide is present in an amount of about 0.2 to 4% by weight based on the weight of the polymerizable resin, and more preferably it is present in an amount of about 0.5 to 1.5% by weight based on the weight of the resin.

It has been found that the opaquing filler used in the present invention must have a hydrophobic surface. This may be provided in accordance with a number of conventional methods, although a particularly suitable technique involves treating the opaquing filler with a conventional silane. For example, the procedure described in U.S. Pat. No. 3,066,112, incorporated herein by reference, may be used to treat the filler with a reactive organosilane material. A particularly useful reactive organosilane for this purpose is gamma-methacryloxypropyltrimethoxysilane ("A-174", commercially available from Union Carbide).

The suspending agent used in the present invention is preferably sub-micron flocculated silica, although any inert, non-toxic, non-irritating filler of sub-micron size may also be used. A particularly useful material has been found to be sub-micron flocculated silica which is commonly available (e.g. "Cab-O-Sil", commercially available from Cabot Corporation; "Aerosil", commercially available from Degussa, Inc.).

It has also been found that the suspending agent must have a hydrophobic surface in order to produce the results desired in the present invention. If the suspending agent does not already have a hydrophobic surface this may be provided in the same manner as used to render the opaquing filler hydrophobic. Preferably such type of suspending agent is treated with a reactive organosilane material.

The amount of suspending agent used in the compositions of the invention is in the range of about 1 to 10% by weight based on the weight of the polymerizable resin system, depending upon the viscosity of the composition. Because the final composition must have a viscosity not greater than about 600 centipoise (preferably 100 to 400 centipoise), the amount of suspending agent used must not be so great as to increase the viscosity of the final composition beyond 600 centipoise. When using sub-micron flocculated silica it has been found that an amount of about 2 to 5% (more preferably 2 to 3%) by weight, based on the weight of the resin, produces particularly good results.

The catalyst which is used in the present invention is a free-radical-generating catalyst when the polymerizable resin is polymerizable by means of free-radical mechanism. A particularly suitable catalyst is benzoyl peroxide, although other peroxide catalysts may also be used. It is typically included in the appropriate composition in an amount of about 0.7 to 2% by weight of the resin present, with 1 to 1.5% by weight being preferred.

The accelerator which is used in this invention may be any of those typically used in dental restorative systems for reaction with a free-radical-generating catalyst. Particularly useful accelerators are tertiary amines such as N,N-dimethyl-p-toluidine and dihydroxyethyl-p-toluidine. The accelerator is normally present in the appropriate composition in an amount of about 1.5 to 3% by weight based on the weight of resin. More preferably the accelerator is present in an amount of about 2 to 2.5% by weight based on resin.

The compositions of the invention also preferably contain small amounts of inhibitor, U.V. absorbers, or the like which are conventional additives in dental restorative materials based on polymerizable resins. It is also possible, if desired, to add materials such as fluoride salts or other common prophylactic or therapeutic agents.

The compositions of the invention are typically prepared by first mixing together the polymerizable resin, inhibitors, U.V. absorbers, and accelerator (or catalyst, depending upon which part of the composition is being prepared). Then the hydrophobic opaquing filler and hydrophobic suspending agent are mixed in under conditions of high shear until a homogeneous dispersion is obtained.

The invention is further illustrated by means of the following non-limiting examples in which the term "parts" refers to parts by weight, unless otherwise indicated.

EXAMPLE 1

Part A of a two-part discernible pit and fissure sealant is prepared by mixing together the following ingredients, in the amounts stated, in a Waring blender.

| Ingredient | Parts |
| --- | --- |
| Bis-GMA resin | 45.48 |
| Triethyleneglycol dimethacrylate | 50.20 |
| Dihydroxyethyl-p-toluidine | 2.40 |
| Silane-treated titanium dioxide | 2.13 |
| Hydrophobic sub-micron silica | 6.38 |
| Inhibitor | 0.12 |
| U.V. absorber | 1.8 |

The resulting composition exhibited a viscosity of about 700 centipoise and was shelf-stable for prolonged periods.

The hydrophobic sub-micron silica had a primary particle size of 10–30 millimicrons and is commercially available from Degussa, Inc. under the name "Aerosil R-972".

The titanium dioxide used in this example had a median particle diameter of 0.21 micron and was treated with an organosilane ("A-174", available from Union Carbide) by adding 89.4 parts of titanium dioxide to 5 parts of toluene (which contained 4 parts of the organosilane in solution) and 1.6 parts of processing aid ("Aerosil R-972"), after which the material was blended in a "PK" blender for approximately 30 minutes. The material was dried in trays at 100–110° C. for 3 hours.

Part B of the two-part discernible pit and fissure sealant is prepared by mixing together the following ingredients, in the amounts stated:

| Ingredient | Parts |
| --- | --- |
| Bis-GMA resin | 51.42 |
| Triethyleneglycol dimethacrylate | 46.58 |
| Benzoyl Peroxide | 1.13 |
| U.V. absorber | 0.8 |
| Inhibitor | 0.007 |

Thus, Part B in this example does not contain either opaquing filler or suspending agent and has a viscosity in the range of about 200 to 300 centipoise.

A very effective pit and fissure sealant is obtained by mixing approximately equal volumes of Part A and Part B and immediately applying such mixture (having a viscosity below 600 centipoise) to occlusal tooth surfaces which have been etched with a 30–40% phosphoric acid solution in conventional manner. The sealant is hardened in a few minutes.

If desired, Part B of this example may also contain hydrophobic opaquing filler and hydrophobic suspending agent, in which case the amount of these materials in Part A should be reduced accordingly so that the viscosity of the Part A/Part B mixture is not greater than 600 centipoise.

EXAMPLE 2

To demonstrate the stability of Part A of Example 1, a sample of such material is placed in a tube (10×75 mm.) and centrifuged. After centrifuging for one hour the titanium dioxide is uniformly suspended throughout the entire height (75 mm.) of the sample (i.e. there is no separation or settling of the opaque filler). After an additional seven hours of centrifuging, the titanium dioxide is uniformly suspended throughout 74 mm. of the sample (i.e. there is essentially no settling or separation).

EXAMPLE 3

Part A of Example 1 is prepared again except that the titanium dioxide is not treated with the organosilane to render it hydrophobic. A sample of the composition is placed in a tube (10×75 mm.) and centrifuged. After one hour a considerable portion of the titanium dioxide has settled toward the bottom of the tube, and after an additional seven hours of centrifuging the titanium dioxide has settled to a height of 15 mm.

Repeating Example 3 using sub-micron silica which is not hydrophobic shows similar results (i.e. the titanium dioxide does not remain stably dispersed on centrifuging).

EXAMPLE 4

Part A of Example 1 is prepared again except that no sub-micron silica is included in the composition. A sample of the composition is placed in a tube (10×75 mm.) and centrifuged. After one hour the titanium dioxide has settled to a height of only 3 mm. Repeating this example using titanium dioxide which has not been silane treated produces similar results.

EXAMPLE 5

Part A of Example 1 is prepared again except that the sub-micron silica is not of the hydrophobic type. A sample of the composition is placed in a tube (10×75 mm.) and centrifuged. After one hour there is no observable settling or separation of the titanium dioxide. However, after an additional seven hours of centrifuging the titanium dioxide has settled to a height of only 15 mm.

What is claimed is:

1. A manufacture adapted for use in filling and sealing pits and fissures in tooth surfaces, said manufacture being composed of two fluid materials, each having a viscosity in the range of about 200 to 600 centipoise, disposed in separate containers from which a dentist may dispense necessary amounts of material which when mixed together will produce a sealant which is discernible on tooth surfaces, the material in the first of said containers consisting essentially of: polymerizable resin system containing acrylic monomer, finely divided hydrophobic opaquing filler present in an amount of about 0.1 to 5% by weight based on the weight of said resin system, hydrophobic suspending agent present in an amount of about 1 to 10% by weight based on the weight of said resin system, and free-radical-generating catalyst for said system; the material in the second of said containers consisting essentially of: polymerizable resin system containing acrylic monomer, finely divided hydrophobic opaquing filler present in an amount of about 0.1 to 5% by weight based on the weight of said resin system, hydrophobic suspending agent present in an amount of about 1 to 10% by weight based on the weight of said resin system, and accelerator reactive with said catalyst in the material of said first container to cause generation of free radicals in sufficient quantity to produce polymerization of said resin system on a tooth surface.

2. A composition adapted for filling and sealing pits and fissures in tooth surfaces in accordance with claim 1, wherein said opaquing filler comprises silane-treated titanium dioxide present in an amount of about 0.2 to 4% by weight based on the weight of said resin system.

3. A composition adapted for filling and sealing pits and fissures in tooth surfaces in accordance with claim 2, wherein said titanium dioxide has a particle size in the range of about 0.1 to 2 microns and is present in an amount of about 0.5 to 1.5% by weight based on the weight of said resin system.

4. A composition adapted for filling and sealing pits and fissures in tooth surfaces in accordance with claim 1, wherein said suspending agent comprises silane-treated sub-micron silica present in an amount of about 3 to 6% by weight based on the weight of said resin system.

5. A composition adapted for filling and sealing pits and fissures in tooth surfaces in accordance with claim 1, wherein said resin system comprises a mixture of Bis-GMA and dimethacrylate monomers.

6. A fluid composition adapted for discernible filling and sealing pits and fissures in tooth surfaces, said composition comprising a polymerizable resin system containing acrylic monomer, finely divided hydrophobic opaquing filler present in an amount of about 0.1 to 5% by weight based on the weight of said resin system, and hydrophobic suspending agent present in an amount of about 1 to 10% by weight based on the weight of said resin system.

7. A fluid composition in accordance with claim 6, wherein said composition further contains free-radical-generating catalyst.

8. A fluid composition in accordance with claim 6, wherein said composition further contains accelerator which is reactive with free-radical-generating catalyst.

9. A method for filling and sealing pits and fissures in tooth surfaces comprising the steps of
(a) applying to said tooth surfaces a composition comprising a polymerizable resin system, finely divided hydrophobic opaquing filler present in an amount of about 0.1 to 5% by weight based on the weight of said resin system, and hydrophobic suspending agent present in an amount of about 1 to 10% by weight based on the weight of said resin system, said composition having a viscosity not greater than about 600 centipoise when applied to said tooth surfaces; and
(b) hardening said composition in situ to produce a discernible coating.

10. A method in accordance with claim 9, wherein said composition is a mixture of two fluid materials, each having a viscosity in the range of about 200 to 600 centipoise, which are mixed together in approximately equal proportions prior to being applied to said tooth surfaces, wherein each of said materials contains polymerizable resin, opaquing filler and suspending agent, and wherein one of said materials further contains free-radical-generating catalyst and the other of said materials further contains accelerator reactive with said catalyst to cause generation of free radicals in sufficient quantity to produce polymerization of said resin system on said tooth surfaces.

11. A method in accordance with claim 10, wherein said opaquing filler comprises silane-treated titanium dioxide present in each of said fluid materials in an amount of about 0.2 to 4% by weight based on the weight of said resin.

12. A method in accordance with claim 11, wherein said titanium dioxide has a particle size in the range of about 0.1 to 2 microns and is present in an amount of about 0.5 to 1.5% by weight based on the weight of said resin.

13. A method in accordance with claim 10, wherein said non-opaque filler comprises silane-treated silica present in an amount of about 3 to 6% by weight based on the weight of said resin.

14. A method in accordance with claim 10, wherein said polymerizable resin comprises a mixture of Bis-GMA and dimethacrylate monomers.

15. A method in accordance with claim 9, wherein said composition is in the form of first and second fluid materials which are mixed together prior to being applied to said tooth surfaces, wherein said first material contains polymerizable resin, wherein the said second fluid material contains polymerizable resin, opaquing filler, and suspending agent; and wherein one of said first and second fluid materials further contains free-radical-generating catalyst and the other of said fluid materials contains accelerator reactive with said catalyst to cause generation of free radicals in sufficient quantity to produce polymerization of said system on said tooth surfaces.

* * * * *